United States Patent [19]

Diederich

[11] Patent Number: 6,040,471
[45] Date of Patent: Mar. 21, 2000

[54] METHOD FOR PREPARING CERTAIN ACETONITRILES

[75] Inventor: Ann Marie Diederich, Downington, Pa.

[73] Assignee: SmithKline Beecham Corporation, Philadelphia, Pa.

[21] Appl. No.: 09/173,268

[22] Filed: Oct. 15, 1998

Related U.S. Application Data

[63] Continuation of application No. 08/952,255, filed as application No. PCT/US96/07108, May 16, 1996, abandoned.

[30] Foreign Application Priority Data

May 17, 1995 [GB] United Kingdom ................... 9509930

[51] Int. Cl.[7] .................................................. C07C 253/00
[52] U.S. Cl. ............................................ 558/315; 558/351
[58] Field of Search ...................................... 558/315, 351

[56] References Cited

PUBLICATIONS

Fieser et al, "Reagents for Organic Synthesis", p. 1047, 1972.

*Primary Examiner*—Joseph K. McKane
*Assistant Examiner*—Joseph Murray
*Attorney, Agent, or Firm*—James M. Kanagy; Charles M. Kinzig

[57] ABSTRACT

This invention relates to a process for making certain acetonitriles.

4 Claims, No Drawings

METHOD FOR PREPARING CERTAIN ACETONITRILES

This is a continuation of application Ser. No. 08/952,255 filed Nov. 14, 1997 now abandoned. which is a 371 of PCT/0596/07108 filed May 16, 1996.

SCOPE OF THE INVENTION

This invention relates to a method for converting benzaldehydes to the corresponding cyanohydroxymethylbenzene analogs and for subsequently reducing those compounds.

BACKGROUND OF THE INVENTION

The chemistry, isolation process and compounds of this invention are all useful in preparing certain end products which are useful pharmaceutical agents. More specifically this invention relates to intermediates and means for preparing and isolating intermediates which can be used to prepare certain known compounds having the following general structure

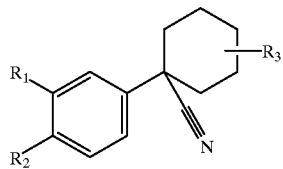

where $R_1$ and $R_2$ are exemplified by ether or thio-ether functionalities and $R_3$ is any one of a number of radicals of which a carboxylate is but one example. Compounds of these types can be found in the literature, more particularly in published patent applications such as, for example, PCT/US93/01990 published as WO93/19748, PCT/US93/02325 published as WO93/19750, PCT/US93/02516 published as WO93/19751, PCT/US93/01988 published as WO93/19747, PCT/US93/01991 published as WO93/19749 and PCT/US93/02230 published as WO93/19720. Of greatest interest are the acetonitriles disclosed in PCT/US93/01991. These compounds are all useful in treating a variety of disease states. In particular they are useful for treating allergic and inflammatory diseases and for inhibiting the production of Tumor Necrosis Factor (TNF).

The compounds and processes of this invention are useful in making the afore mentioned pharmaceutical entities in so far as they have a —CN group on the cycloalkyl ring at the carbon forming a bond with the benzene ring carbon.

SUMMARY OF THE INVENTION

This invention relates to a process for converting a benzaldehyde to a cyanohydrin in an aqueous medium comprising first adding about 1 to 1.5 equivalents of an alkali metal bisulfite to a solution of the benzaldehyde, then adding an alkali metal cyanide to this mixture, and then adding a second charge of about 1.5 to 2.5 equivalents of the alkali metal bisulfite while maintaining the pH between about 6.5 to 7.5 and maintaining the temperature of the reaction mixture at between about 0 and 30° C.
General Embodiments While the illustrations given herein are specific to isovanillin and the derivatives made therefrom, the chemistry disclosed herein can be used with other benzaldehydes.

The compound and chemistry of this invention can be used to make cyanohydrins. These cyanohydrins are intermediates in the path for making certain bicyclic compounds as noted above. The compounds made by the chemistry of this invention are intermediates in the processes outlined in the several PCT applications set out above, namely PCT/US93/01990 published as WO93/19748, PCT/US93/02325 published as WO93/19750, PCT/US93/02516 published as WO93/19751, PCT/US93/01988 published as WO93/19747, PCT/US93/01991 published as WO93/19749 and PCT/US93/02230 published as WO93/19720.

In general, this process comprises dissolving a benzaldehyde in an aqueous medium, preferably just water, then adding at least about an equivalent or more of an alkali metal bisulfite. Sodium is the preferred alkali metal cation. The temperature of the reaction mixture should be maintained at about room temperature during the addition of the bisulfite. Stirring or some form of mixing may be begun during the addition of the bisulfite, and is continued for about 15 minutes to upwards of an hour thereafter. A white solid may appear on additions of the bisulfite and during the period of mixing. The temperature of the mixture should be maintained at about room temperature during this period as well. After the aforesaid mixing period, the reaction mixture is cooled to between about 0 to 20° C. Once this is accomplished, an aqueous solution of alkali metal cyanide is added, preferably over a period of about 1 to 5 hours. At least about 1.5 and 2.5 equivalents of the cyanide salt are added. The preferred cation is potassium, though sodium or one of the other monovalent alkali metal ions could be used as well, provided it forms water soluble salts. During the addition of the cyanide, the temperature of the mixture is maintained at between about 0 and 20° C. by some cooling means. Stirring or some form of mixing is used to keep the mixture in motion during the addition of the cyanide. Once all of the cyanide has been added the pH of the mixture will have become basic. A pH of up to about 9 is not uncommon. Thereafter additional alkali metal bisulfite is added portionwise or in one batch. In addition, the pH of the mixture is adjusted to between about pH 6.5 and 7.5; the additional bisulfite can effect this result or an acid can be added to the reaction vessel to bring the pH down into this range if the addition of the bisulfite is not sufficient to effect this change or it is desired to add a proton source to insure said pH range is attained. This pH range effectively shifts the equilibrium of the reaction to the cyanohydrin form. This pH range may also be optimal in-so-far as product stability is concerned. This second charge of bisulfite is preferably the same salt form as was initially added to the solution containing just the benzaldeyde. About 1.5 to 2.5 equivalents of the bisulfite should be added during the course of this second addition. Again the temperature of the reaction mixture is maintained at between about 0 and 30° C., though a range of 0 to 25° C. is more preferred. Once the second batch of bisulfite has been completely added, the reaction mixture is stirred long enough to effect completion of the reaction which is determined by some means such as a separatory means, e.g., thin layer chromatography or HPLC. The disappearance of the starting benzaldehyde or a repeating very small quantity of the substrate can be taken to mean the reaction has gone to completion or is at its final equilibrium.

The following examples are being provided to exemplify the invention. They are only examples and should not be read as limiting the invention in any manner. Reference is made to the claims for what is reserved to the inventor(s) hereunder.

EXAMPLES

Example 1

Preparation of 4-(Cyanohydroxy)methyl-2-hydroxy-1-methoxybenzene

A 5 L 3-neck flask was equipped with a thermometer, an overhead air-stirrer, an addition funnel, and a cooling bath.

The flask was charged with 1175 mL of water and 250 g isovanillin (1.64 mol, 1.0 eq.). A 225 g portion of sodium bisulfite (2.2 mol, 1.3 eq.) was then added as a solid while the temperature was maintained at 22° C. The solution was stirred for 30 minutes and became a thick white slurry and then the reaction was cooled to 14° C.

A solution of potassium cyanide (214 g, 3.29 mol, 2.0 eq.) in 330 mL of water was charged to the addition funnel. This solution was added to the 5 L flask over 2 hours. The cooling bath was adjusted in order to maintain the temperature between 14 and 18° C. The reaction remained thick and white throughout the addition. When the addition was complete, sodium bisulfite (420 g, 4.0 mol, 2.46 eq.) was added at once as a solid. During this addition, the reaction temperature was maintained between 16 and 22° C. The reaction was stirred until complete by HPLC analysis (Supelco LC ABZ; Solvent: A—0.1% phosphoric acid/water, B—0.1% phosphoric acid/acetonitrile; Isocratic 10% B; 2.0 mL/min; Detector UV 230 nm).

The temperature was maintained at 8 to 12° C. throughout the entire workup. To the reaction flask was added 1 L of cold water and 1 L of cold t-butylmethyl ether. This solution was stirred until all solids dissolved. The layers were separated. The aqueous layer was then extracted three times with cold t-butylmethylether (700 mL each time). The combined t-butylmethylether volumes were extracted once with 250 mL of brine. Acetic acid (50 mL) was added to the t-butylmethylether (to acidify and stabilize the cyanohydrin). The solution was distilled to remove the ether while adding acetic acid as a replacement solvent (900 mL total). The final solution was then used "as is" in the next step.

Example 2

Preparation of 4-Cyanomethyl-2-hydroxy-1-methoxybenzene

A 12 L round bottom flask was fitted with an overhead stirrer, a nitrogen line and a thermometer. The system was charged with 2.5 L of glacial acetic acid, 10 mL of HI and 287.6 g of $H_3PO_3$. This mixture was stirred and heated to 80° C. Then 2.8 L of a solution of 4-(cyanohydroxy)methyl-2-hydroxy-1-methoxybenzene (prepared according to Example 1) was added at one time. This solution was stirred with heating, reaching a temperature of about 115° C. before beginning to cool; the reaction was essentially complete in 2 hours. Removal of the solvents was then begun using vacuum distillation (water aspirator) while maintaining the bath at 50° C. Most of the acetic acid was removed by this method. To further effect removal of the acetic acid, toluene was added (3.4 L) to form an azeotrope (about 70/30 toluene/acetic acid). The captioned compound was then partitioned between toluene and aqueous sodium acetate. Then the toluene layer was treated with a thiosulfate solution, and finally with brine.

Example 3

Second Preparation of 4-(Cyanohydroxy)methyl-2-hydroxy-1-methoxybenzene

A 2-L three-necked flask was charged with 300 mL of water and 100 g of isovanillin (0.657 mol, 1.0 eq.) (pH=5.3). The solution was brought to 19° C., then sodium bisulfite (88.8 g, 0.854 mol, 1.3 eq.) was added as a solid. The solution was stirred for 60 minutes during which time the temperature increased to 24° C. and decreased back to 19° C. (pH=4.2). The solution was then cooled to 4° C. in an ice bath. An addition funnel was charged with potassium cyanide (85.6 g, 1.31 mol, 2.0 eq.) dissolved in 133 mL of water. The potassium cyanide solution was added to the reaction over 90 minutes. The temperature was maintained between 4° C. and 7° C. during the addition. The solution thickened and whitened during the addition of the cyanide (pH=8.9). When the addition was complete, 280 mL of t-butylmethyl ether was added to form two layers which partitioned the product and starting materials (most of the product was in the organic layer). At this point, additional sodium bisulfite was added in four parts. A total of 170.8 g (1.64 mol, 2.5 eq) was added over 12 minutes in approximately 42 g per charge. The temperature increased to 14° C. during this time. The reaction was analyzed after each charge. The reaction was deemed complete by HPLC analysis (pH=6.5 to 7.5) between the second and fourth charge.

The solution was cooled to 10° C. Then 220 mL of t-butylmethyl ether and 500 mL of water was added. The solution was stirred until all solids dissolved. The layers were separated, then the aqueous layer was extracted with t-butylmethyl ether twice (300 mL each time). The combined ether layers were extracted once with 200 mL of brine. Acetic acid (25 mL) was added to the organic layer, then the solvent was evaporated under reduced pressure until a white solid was obtained. The cyanohydrin was stored as a solution in 400 mL of acetic acid. The isolated yields of the cyanohydrin for this reaction sequence ranged from 90–99%.

What is claimed is:

1. A process for converting a benzaldehyde to a cyanohydrin in an aqueous medium comprising first adding about 1 to 1.5 equivalents of an alkali metal bisulfite to a solution of the benzaldehyde, then adding an alkali metal cyanide to this mixture, and then adding a second charge of about 1.5 to 2.5 equivalents of the alkali metal bisulfite while maintaining the pH between about 6.5 to 7.5 and maintaining the temperature of the reaction mixture at between about 0 and 30° C.

2. The method of claim 1 wherein the medium is water.

3. The method of claim 1 wherein the alkali metal cyanide is potassium cyanide.

4. The method of claim 1 wherein the alkali metal bisulfite is sodium bisulfite.

* * * * *